United States Patent [19]

Holls et al.

[11] Patent Number: 5,372,139

[45] Date of Patent: Dec. 13, 1994

[54] METHOD FOR SUPPRESSING A MATERNAL ELECTROCARDIOGRAM SIGNAL FROM A FETAL ELECTROCARDIOGRAM SIGNAL OBTAINED WITH INVASIVE AND NON-INVASIVE TECHNIQUES USING AN ALMOST PURE MATERNAL ELECTROCARDIOGRAM SIGNAL AS A TRIGGER

[75] Inventors: William M. Holls, Knox; Steven L. Horner, Davidson, both of Tenn.

[73] Assignee: Paul Benjamin Crilly, Knoxville, Tenn.

[21] Appl. No.: 96,669

[22] Filed: Jul. 26, 1993

Related U.S. Application Data

[63] Continuation-in-part of Ser. No. 719,377, Jun. 24, 1991, abandoned.

[51] Int. Cl.$^5$ ................................................ A61B 5/02
[52] U.S. Cl. ...................................... 128/698; 128/708
[58] Field of Search ............... 128/696, 698, 708, 700, 128/701

[56] References Cited

U.S. PATENT DOCUMENTS

| | | | |
|---|---|---|---|
| 4,456,959 | 6/1984 | Hirano et al. | 364/417 |
| 4,519,396 | 5/1985 | Epstein et al. | 128/698 |
| 4,569,356 | 2/1986 | Kyozuka | 128/698 |
| 4,573,479 | 3/1986 | Tuccillo | 128/698 |
| 4,781,200 | 11/1988 | Baker | 128/670 |
| 4,945,917 | 8/1990 | Akselrod et al. | 128/696 |
| 4,951,680 | 8/1990 | Kirk et al. | 128/698 |
| 4,961,428 | 10/1990 | Nikias et al. | 128/699 |
| 4,974,598 | 12/1990 | John | 128/696 |

OTHER PUBLICATIONS

Widrow, Glover, et al, "Adaptive Noise Canceling: Principals and Applications", *Proc. of the IEEE*, vol. 63, No. 12, Dec. 1975, pp. 1692–1716.

D. Adam and D. Shavit, "Complete Fetal ECG Morphology Recording by Synchronized Adaptive Filtration", *Med. & Biol. Eng. & Comput.*, vol. 28, pp. 287–292, Jul. 1990.

E. R. Ferrara and B. Widrow, "Fetal Electrocardiogram Enhancement by Time Sequences Adaptive Filtering," *IEEE Trans. Biomed. Eng.*, vol. BME-29, No. 6, pp. 458–460, Jun. 1982.

R. L. Longini, T. A. Reichert, J. M. C. Yu, and J. S. Cromley, "Near Orthogonal Basis Function: A Real Time Fetal ECG Technique", *IEEE Trans. on Biomedical Eng.*, vol. BME-24, No. 1, pp. 39–43, Jan. 1977.

(List continued on next page.)

*Primary Examiner*—William E. Kamm
*Assistant Examiner*—Scott M. Getzow
*Attorney, Agent, or Firm*—Pitts and Brittian

[57] ABSTRACT

A method (10) for suppressing the maternal electrocardiograph (MECG) signal from a composite abdominal ECG including an MECG signal, an fetal ECG (FECG) signal and noise to obtain a substantially MECG-free FECG trace. The method (10) of the present invention includes the placement of a plurality of electrodes (26) about the periphery of the mother to detect a substantially pure MECG (12) and a composite MECG+FECG signal (14). A scalp electrode (32A), which is invasive to the fetus (72), and an intrauterine catheter electrode (32B), which is non-invasive to the fetus (72), may be alternately used to detect the signal (14), both electrodes (32A,32B) being invasive to the mother. A preprocessor (34) converts the signals (12,14) obtained by the individual electrodes (26,32A,32B) attached to, or invasive to, the mother (70) into appropriate electrical or digital signals for MECG suppression, and selectively performs a filtering operation to remove noise and other distortions. The MECG suppression is achieved by using a substantially pure MECG trace (12) as a trigger signal to calculate an MECG complex template (18) which is subtracted from the composite signal (14) using the MECG trace (12) to align the MECG complex template (18) with each MECG complex (16) in the composite signal (14).

18 Claims, 5 Drawing Sheets

OTHER PUBLICATIONS

P. Bergveld, A. J. Knolling, and J. H. J. Peuscher, "Real Time Fetal ECG Recording", *IEEE Trans. on Biomedical Eng.*, vol. BME-33, No. 5, pp. 505-509, May 1986.

D. Callaerts, et al, "Comparison of SVD Methods to Extract the Fetal Electrocardiogram from Cutaneous Electrodes Signals", *Med. & Biol. Eng. & Comput.*, vol. 28, pp. 217-224, May 1990.

S. Abboud, G. Barkai, S. Mashiach, and D. Sadeh, "Quantification of the Fetal Electrocardiogram Using Averaging Technique", *Comput. Biol. Med.*, vol. 20, pp. 147-155, Feb. 16, 1990.

S. Cerutti, et al, "Variability Analysis of Fetal Heart Rate Signals as Obtained from Abdominal Electrocardiographic Recordings", *J. Perinat. Med.*, 14, pp. 445-452, 1986.

J. H. Nagel, "Progresses in Fetal Monitoring by Improved Data Acquisition", *IEEE Eng. Med. & Biol. Mag.*, pp. 9-13, Sep. 1984.

T. F. Oostendrop, et al, "The Potential Distribution Generated by the Fetal Heart at the Maternal Adbomen", *J. Perinat. Med.*, 14, pp. 435-444, 1986.

N. J. Randall, et al, "Detection of the Fetal ECG during Labour by an Intrauterine Probe", *J. Biomed. Eng.*, vol. 10, pp. 159-164, Apr., 1988.

T. H. Strong, et al, "The Intrauterine Probe Electrode", *Am. J. Obstet. Gynecol.*, 164, pp. 1233-1234, May, 1991.

A. Masaki, et al., "Neural Networks in CMOS: a Case Study", *Circuits and Devices*, pp. 13-17, Jul., 1990.

M. F. Kelly, et al., "The Application of Neural Networks to Myoelectric Signal Analysis: A Preliminary Study", *IEEE Transactions on Biomedical Engineering*, vol. 37, No. 3, pp. 221-230, Mar., 1990.

A. G. Favret, et al., "Evaluation of Autocorrelation Techniques for Detection of the Fetal Electrocardiogram", *IEEE Transactions on Bio-Medical Engineering*, vol. BME-13, No. 1, pp. 37-43, Jan., 1966.

J. H. Van Bemmel, "Detection of Weak Foetal Electrocardiograms by Autocorrelation and Crosscorrelation of Envelopes", *IEEE Transactions on Bio-Medical Engineering*, vol. BME-15, No. 1, pp. 17-23, Jan., 1968.

P. Bergveld, "A New Technique for the Suppression on the MECG", *IEEE Transactions on Bio-Medical Engineering*, vol. BME-28, No. 4, pp. 348-357, Apr., 1981.

S. Azevado, et al., "Abnominal-Lead Fetal Electrocardiographic R-Wave Enhancement for Heart Rate Determination", *IEEE Transactions on Bio-Medical Engineering*, vol. BME-27, No. 5, pp. 255-260, May, 1980.

M. Yelderman, "ECG Enhancement by Adaptive Cancellation of Electrosurgical Interference", *IEEE Transactions on Bio-Medical Engineering*, vol. BME-30, No. 7, pp. 392-398, Jul., 1983.

C. Laxer, et al., "The Use of Unipolar Epicardial QRS Potentials to Estimate Myocardial Infarction", *IEEE Transactions on Bio-Medical Engineering*, vol. BME-30, No. 7, pp. 392-398, Jul., 1983.

M. L. Ahlstrom, et al., "Digital Filters for Real-Time ECG Signal Processing Using Microprocessors", *IEEE Transactions on Bio-Medical Engineering*, vol. BME-32, No. 9, pp. 708-713, Sep., 1985.

P. Bergveld, et al., "Real-Time Fetal ECG Recording", *IEEE Transactions on Bio-Medical Engineering*, vol. BME-33, No. 5, pp. 505-509, May, 1986.

S. B. Kwatra, et al., "A New Technique for Monitoring Heart Signals—Part I: Instrumentation Design", *IEEE Transactions on Bio-Medical Engineering*, vol. BME-33, No. 1, pp. 35-41, Jan., 1986.

S. B. Kwatra, et al., "A New Technique for Monitoring Heart Signals—Part II: Orthogonal Lead Extraction", *IEEE Transactions on Bio-Medical Engineering*, vol. BME-33, No. 1, pp. 1-9, Jan., 1986.

M. Okada, "A Digital Filter for the QRS Complex Detection", *IEEE Transactions on Bio-Medical Engineering*, vol. BME-26, No. 12, pp. 700-703, Dec., 1979.

S. D. Nandedkar, et al., "Special-Purpose Orthonormal Basis Functions-Applications to Motor Unit Action Potentials", *IEEE Transactions on Biomedical Engineering*, vol. BME-31, No. 4, pp. 374-377, Apr., 1984.

M. R. Neuman, "Electronic Monitoring of the Fetus", *Clinics in Perinatology*, vol. 10, No. 1, pp. 237-252, Feb., 1983.

Y. Murata, "Advances on the Horizon", *Clinics in Perinatology*, vol. 9, No. 2, pp. 433-441, Jun., 1982.

X. Lecoutour, "Continuous Twenty-Four Hour Recording of the Fetal Cardiac Rhythm During Normal Pregnancies", *Int. J. Gynaecol. Obstet.*, 22, pp. 358-388, 1984.

METHOD FOR SUPPRESSING A MATERNAL ELECTROCARDIOGRAM SIGNAL FROM A FETAL ELECTROCARDIOGRAM SIGNAL OBTAINED WITH INVASIVE AND NON-INVASIVE TECHNIQUES USING AN ALMOST PURE MATERNAL ELECTROCARDIOGRAM SIGNAL AS A TRIGGER

This application in part discloses and claims subject matter disclosed in our earlier filed pending application Ser. No. 07/719,377 filed on Jun. 24, 1991 now abandoned.

TECHNICAL FIELD

This invention relates to the field of monitoring fetal heart activity. More specifically, this invention relates to a method of enhancing, analyzing and interpreting a complete fetal electrocardiogram (FECG) signal, or any part thereof, from sensors placed on the mother about the periphery or internally using an almost pure maternal electrocardiogram (MECG) as a trigger to suppress the MECG portion of a composite MECG+FECG signal.

BACKGROUND ART

In the field of prenatal care and treatment, it is well known that during the development of a fetus and throughout childbirth, it is often desirable and necessary to monitor the fetal electrocardiogram (FECG, also called fetal electrokardiogramm, or EKG). One period of an ECG is called a complex and is composed of a P wave, QRS waves and a T wave. The ECG or ECG trace is composed of several complexes that are somewhat periodic in time.

It is well known that the ECG waveform or the fetal heart rate is used to monitor the development and delivery of the fetus. An FECG can be used to alert the physician when the development or delivery is not proceeding satisfactorily, as indicated by an abnormal increase or decrease in fetal heart rate or an abnormal FECG, so that appropriate corrective measures may be taken. It is also known that historical ECG data can be used to correlate with fetal outcomes.

The FECG can be obtained non-invasively by placing electrodes on the abdominal surface area or invasively by placing electrodes inside the uterus of the mother. Two types of invasive electrodes, both of which are invasive to the mother, include a fetal scalp electrode which is also invasive to the fetus and an intrauterine catheter electrode which is non-invasive to the fetus.

In practice it is relatively difficult to non-invasively observe the FECG. This is due to the fact that the abdominal ECG being taken from the periphery of the mother consists of both the maternal electrocardiogram (MECG) and the FECG. This composite signal may also contain a relatively large amount of noise from muscle and breathing movements and other interferences. This interference can be especially strong during the delivery process.

It is well known that the placement of the ECG leads for reliable FECG sensing is a relatively difficult task. Thus, a reliable observation and detection of the FECG is made even more difficult. Further contributing to the difficulty of obtaining and reliably observing the FECG is the relative weakness of the FECG signal as compared to the strength of the MECG signal. The signal strength of the MECG can be somewhat similar or many times greater than that of the FECG. This is especially a problem when the maternal and fetal ECG QRS waves are coincident to each other. When such coincidence occurs, the MECG completely overlaps the FECG such that only the MECG signal is observable under usual circumstances.

In the prior art, leads are typically placed on the mother proximate to the fetus to obtain a composite MECG+FECG signal from the mother and the fetus. Leads may also be placed on the mother proximate the maternal heart such that a relatively pure MECG signal may be obtained. Estimates of the FECG are then made using the data obtained from the leads placed proximate the fetus and the leads placed proximate the maternal heart.

Currently there are several known techniques for enhancing the non-invasive abdominal ECG signal(s). These methods include the subtractive, adaptive filtering, orthogonal basis, linear combination, single value decomposition and MECG averaging and correlation.

The subtractive methods are the easiest techniques to implement. Typically the subtractive method is accomplished by trial and error. This heuristic method involves the subtraction of the pure MECG signal from the abdominal ECG by at least one lead at a given time. The result is then an estimate of the FECG at the particular lead. The subtractive technique, however, is limited to cases where the pure MECG is similar in shape and size as the abdominal ECG that contains the FECG. A variation of the subtractive method using first and second derivatives is described in U.S. Pat. No. 4,945,917, issued to S. Akselrod, et al, on Aug. 7, 1990.

The adaptive filtering technique is used to cancel a wide variety of interferences and distortions in signals, including speech signals and the MECG and noise components of the non-invasively- or invasively-obtained ECG signals. The adaptive filtering technique for non-invasive MECG cancellation uses at least one abdominal lead to obtain the FECG signal along with the interfering noise and MECG signal. At least three additional leads from the maternal thoracic area are used as reference inputs to an adaptive filter.

The inputs from the thoracic leads are used to replicate the interfering MECG signal obtained by the abdominal lead or leads through scale factors and this resulting estimate of the MECG of the abdominal lead is used to subtract the abdominal MECG. The output is thus an approximation of the FECG. This technique is described by Widrow, Glover, et al, "Adaptive Noise Canceling: Principals and Applications", *Proc. of the IEEE*, Vol. 63, No. 12, Dec. 1975, pp. 1692-1716.

The adaptive filtering technique for noise suppression has been published by D. Adam and D. Shavit, "Complete Fetal ECG Morphology Recording by Synchronized Adaptive Filtration", *Med. & Biol. Eng. & Comput.*, Vol. 28, pp. 287-292, July 1990 and E. R. Ferrara and B. Widrow, "Fetal Electrocardiogram Enhancement by Time Sequenced Adaptive Filtering," *IEEE Trans. Biomed. Eng.*, Vol. BME-29, No. 6, pp. 458-460, June 1982. The Adam, et al, method uses a Doppler echo-ultrasound signal to determine each of the FECG complex locations in the abdominal ECG and suppresses the noise using this information in an adaptive filter. The Ferrara, et al, technique uses a peak detect on the abdominal ECG signal to determine each FECG complex location and then uses an adaptive filtering algorithm similar to that used by Adam, et al, to improve the signal-to-noise ratio of the FECG. An example of the adaptive filtering technique is described in U.S. Pat. No. 4,781,200 issued to D. A. Baker on Nov. 1, 1988.

The orthogonal basis, linear combination and single value decomposition techniques are similar to the adaptive filtering approach for canceling the MECG by scaling at least three pure MECG signals found on the patient's periphery. These scaling coefficients are calculated through either the Gramm-Schmidt procedure, linear programming, or by single value decomposition. R. L. Longini, T. A. Reichert, J. M. C. Yu, and J. S. Cromley, "Near Orthogonal Basis Function: A Real Time Fetal ECG Technique", *IEEE Trans. on Biomedical Eng.*, Vol. BME-24, no. 1, pp. 39–43, Jan. 1977; P. Bergveld, A. J. Kolling, and J. H. J. Peuscher, "Real Time Fetal ECG Recording", *IEEE Trans. on Biomedical Eng.*, Vol. BME-33, no. 5, pp. 505–509, May 1986; and D. Callaerts, et al, "Comparison of SVD Methods to Extract the Fetal Electrocardiogram from Cutaneous Electrodes Signals", *Med. & Biol. Eng. & Comput.*, Vol. 28, pp. 217–224, May 1990 have reported these techniques. The orthogonal basis and linear combination approaches have been implemented in real-time.

Finally, the MECG averaging and correlation technique has been reported by S. Abboud, G. Barkai, S. Mashiach, and D. Sadeh, "Quantification of the Fetal Electrocardiogram Using Averaging Technique", *Comput. Biol. Med.*, Vol. 20, pp. 147–155, Feb. 16, 1990; S. Cerutti, et al, "Variability Analysis of Fetal Heart Rate Signals as Obtained from Abdominal Electrocardiographic Recordings", *J. Perinat. Med.*, 14, pp. 445–452, 1986; J. H. Nagel, "Progresses in Fetal Monitoring by Improved Data Acquisition", *IEEE Eng. Med. & Biol. Mag.*, pp. 9–13, September 1984; and T. F. Oostendorp, et al, "The Potential Distribution Generated by the Fetal Heart at the Maternal Abdomen", *J. Perinat. Med.*, 14, pp. 435–444, 1986. The MECG averaging and correlation technique obtains MECG cancellation by only using the non-invasive abdominal ECG signal.

MECG averaging and correlation is accomplished by performing a peak detection on the non-invasive abdominal ECG to find the time location of each MECG R wave. The MECG average of the abdominal ECG is then calculated based on the peak detection result. After the MECG average is found, a correlation is performed between the average and the non-invasive abdominal ECG signal to determine the abdominal MECG complex time locations from which the MECG average will be subtracted.

The non-invasive FECG procedure has been in research for many years and there are a few commercially-available monitoring systems that use this procedure. The invasive scalp electrode is extensively available commercially for fetal heart rate monitoring and is commonly used in labor and delivery. Typical of the art are those monitors manufactured by Corometrics Medical Systems and Hewlett Packard. Typically, commercial monitors do not use the intrauterine catheter electrode.

The invasive scalp electrode as discussed above can detect a significant FECG signal such that the fetal heart rate may be determined. However, this electrode is invasive to the fetus also. It is desirable to have an electrode which is invasive to the mother but non-invasive to the fetus. This type of electrode may be called an intrauterine catheter electrode. However, the intrauterine catheter electrode, as compared to the scalp electrode, detects an MECG and the scalp electrode detects minimal MECG signals. N. J. Randall, et al, "Detection of the Fetal ECG during Labour by an Intrauterine Probe", *J. Biomed. Eng.*, Vol. 10, pp. 159–164, April, 1988; and T. H. Strong, et al, "The Intrauterine Probe Electrode", *Am. J. Obstet. Gynecol.*, 164, pp. 1233–1234, May, 1991, have developed their own intrauterine catheter electrodes and have tried to cancel the MECG using signal processing techniques such as adaptive filtering.

Other methods and systems have been devised to monitor FECG signals for prenatal observation and care and throughout childbirth. Typical of the art are those devices disclosed in the following U.S. Patents:

| U.S. Pat. No. | Inventor(s) | Issue Date |
| --- | --- | --- |
| 4,456,959 | T. Hirano, et al | Jun 26, 1984 |
| 4,519,396 | P. Epstein, et al | May 28, 1985 |
| 4,569,356 | S. Kyozuka | Feb 11, 1986 |
| 4,573,479 | M. J. Tuccillo | Mar 4, 1986 |
| 4,951,680 | D. L. Kirk, et al | Aug 28, 1990 |
| 4,961,428 | C. L. Nikias, et al | Oct 9, 1990 |
| 4,974,598 | E. R. John | Dec 4, 1990 |

However, the above patents disclose methods and systems for obtaining an FECG signal using invasive techniques or which rely upon ultrasound, Doppler techniques, and other undesired techniques. In a number of the above-referenced patents, the desired output is the fetal heart rate and not the FECG trace or complex including the P wave, QRS waves and T wave.

Therefore, it is an object of this invention to provide a means for obtaining a clear and accurate FECG trace and complex, or any part thereof.

It is also an object of the present invention to provide a means for obtaining a clear and accurate FECG trace and complex in a manner which is non-invasive to the mother and the fetus.

Another object of the present invention is to provide a means whereby a clear an accurate FECG trace and complex may be obtained by a procedure which is invasive to the mother and which uses electrodes which are invasive or non-invasive to the fetus, the FECG trace and complex being processed in a similar fashion to the non-invasive abdominal ECG trace, such as suppressing the MECG, improving the signal-to-noise ratio of the FECG, and determining the fetal heart rate.

Still another object of the present invention is to provide a means whereby a clear and accurate FECG trace and complex, or any part thereof, may be monitored throughout gestation and delivery.

Yet another object of the present invention is to provide a means for displaying an accurate estimate of a clear and accurate FECG trace and complex, or any part thereof.

Another object of the present invention is to provide means whereby the ECG data acquired may be stored or otherwise processed as desired.

Still another object of the present invention is to provide a means whereby abnormalities in the FECG trace and complex may be detected and an attending physician alerted as to such abnormalities.

Still another object of the present invention is to provide a means whereby ECG data may be obtained to provide fetal heart rate determination using procedures which are non-invasive to the mother or invasive to the mother and non-invasive to the fetus.

DISCLOSURE OF THE INVENTION

Other objects and advantages will be accomplished by the present invention which serves to produce a clear FECG trace and complex, or any part thereof, or to detect the fetal heart rate (FHR). Moreover, in the preferred embodiment the method for suppressing the MECG is designed to process the ECG data received in a selected manner to be used in monitoring the development of a fetus and delivery of the same.

The method for suppressing the MECG of the present invention includes the placement of electrodes sets about the periphery of the mother. In the preferred non-invasive embodiment, a first set of electrodes is placed to obtain an almost pure trigger MECG signal that is almost completely free of low frequency baseline and electromyographic (EMG) noise. EMG noise is generated from muscle activity, whether voluntary or involuntary. Muscle activity causes electrical activity which in turns interferes with the detected MECG.

The trigger MECG signal can be obtained from a lead placement on the thoracic area with a left leg electrode placed slightly toward the posterior thorax area more than normal to reduce low frequency baseline noise, along with an electrode placed on the upper right portion of the thoracic region. A lead placement including one electrode at each of the upper and lower portions of the left or right sides of the thoracic region may alternatively be used. A second set of electrodes is placed to obtain a combined MECG+FECG signal. Each of the leads placed about the periphery of the mother is attached in a non-invasive fashion.

In the preferred embodiment which is invasive to the mother and either invasive or non-invasive to the fetus, electrodes are non-invasively placed on the maternal thoracic area to obtain an almost pure trigger MECG that again is almost free of low frequency baseline and EMG noise. The invasive electrodes are placed in the uterus of the mother to obtain an FECG signal using a scalp electrode which is invasive to the fetus or an intrauterine catheter electrode which is non-invasive to the fetus.

A preprocessor is provided for processing the signals obtained from the mother. The preprocessor will typically consist of an ultra low noise preamplifier to amplify the non-invasive abdominal ECG or invasively-obtained ECG signal(s). The preprocessor further acts to filter noise and other distortions by limiting bandwidth of the ECG signals. The preprocessor also receives the signals and converts each into an appropriate digital signal which may undergo further preprocessing such as standard digital filtering and more specialized adaptive filtering. The original signals that are digitized will also be stored for future reference and analysis before digital filtering.

The signals from the preprocessor are input into an MECG filtering algorithm. The MECG filtering algorithm cancels the MECG by using the almost pure MECG signal as a trigger to accurately determine the time location of each MECG complex in the non-invasive abdominal ECG or the signal obtained from the invasive scalp electrode or intrauterine catheter electrode. These time or trigger locations are determined first by finding the absolute maximum sample of a block of samples of an almost pure MECG having a selected duration. One-half, or any other appropriate fraction, of this maximum value is used as a threshold for a peak detection algorithm to determine the time location of each R wave in the substantially pure MECG block of samples.

After the approximate time locations of each R wave are determined, a gradient ascending or localized maximum algorithm is used to find the absolute peak of each R wave in the almost pure MECG signal. Next, each of the R wave peak time locations are used to determine the alignment for the MECG average calculated from the MECG+FECG signal. The direct current offset, or d.c. offset, of each abdominal MECG complex is reduced by averaging the first selected number of samples and the last selected number of samples (generally five to fifteen each) of each detected MECG complex of the abdominal ECG. The corresponding average of each MECG complex is then subtracted from each sample of the MECG complex before all of the complexes are averaged together. Next, the relatively d.c. offset-free MECG average is subtracted using the same trigger location as used for calculating the MECG average that was obtained from the pure almost MECG signal. The resulting signal has a significant reduction in the MECG with little distortion to the remaining FECG and other bio-potential signals of the abdominal ECG composite signals.

The MECG free signal is then directed towards a post-processor which may include FECG averaging, adaptive filtering and other signal enhancing techniques. Finally, the processed FECG trace and complex is further introduced into an FECG data processing system for selected analysis in determining fetal heart abnormalities.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

A method for suppressing the maternal electrocardiograph (MECG) of a composite abdominal electrocardiograph (ECG) including an MECG signal, a fetal electrocardiograph (FECG) signal and noise incorporating various features of the present invention is illustrated generally at 10 in the Figures. The composite ECG signal may be obtained through methods which are invasive or non-invasive to the mother. In those methods which are invasive to the mother, the composite ECG may be obtained by methods which are invasive or non-invasive to the fetus. Methods which are invasive both to the mother and the fetus may include the use of a scalp electrode 32A. Methods which are invasive to the mother and non-invasive to the fetus may include the use of an intrauterine catheter electrode 32B. The above invasive and non-invasive methods can be used to obtain fetal heart rate (FHR) information.

Figure 2A:
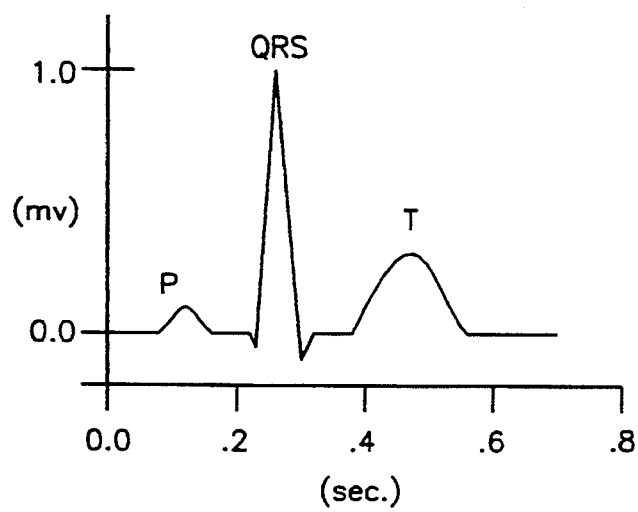
FIG. 2A illustrates an ECG complex composed of a P wave, QRS waves and a T wave.
Figure 2B:
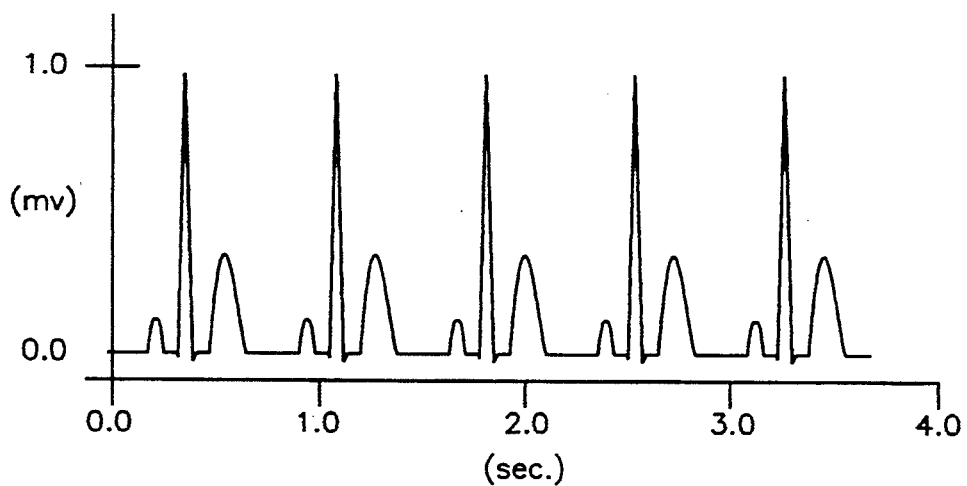
FIG. 2B illustrates a plurality of consecutive ECG complexes combining to form an ECG trace.

One period of an ECG is defined as a complex and is usually composed of a P wave, QRS waves and a T wave, as shown in FIG. 2A. An ECG trace is composed of several complexes that are somewhat periodic in time as illustrated in FIG. 2B.

Figure 1:
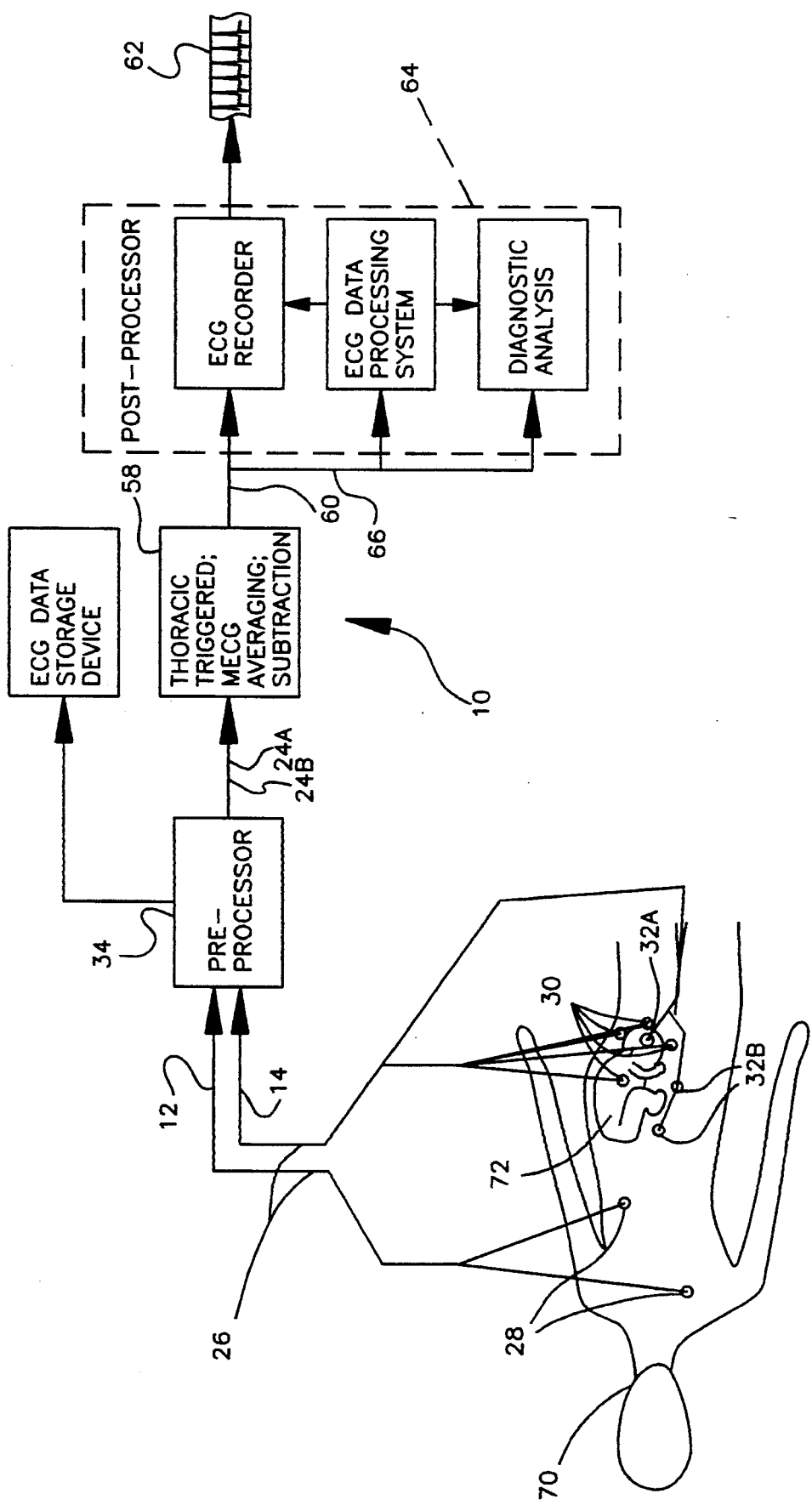
FIG. 1 is a schematic diagram of the method for analyzing maternal and fetal electrocardiogram (MECG and FECG) signals constructed in accordance with several features of the present invention.

The method 10 of the present invention is designed for producing a substantially MECG-free FECG trace or any selected portion thereof. As shown in FIG. 1, a preprocessor 34 and a post-processor 64 are incorporated. In the preferred embodiment, the preprocessor 34 includes a low-noise preamplifier and other filtering elements. The post-processor 64 filters the substantially MECG-free FECG trace to improve the signal-to-noise ratio of the FECG and to determine if the development of the fetus 72 and delivery are progressing satisfactorily.

In the method 10 of the present invention, a plurality of sets of electrodes 26 are preferably placed about the maternal periphery to obtain the MECG of the mother 70 and the FECG of the fetus 72. In the preferred embodiment, a first set of electrodes 28 are placed to obtain a substantially pure MECG trace 12. A second set of non-invasive electrodes 30 includes a plurality of leads placed proximate the maternal abdomen to obtain a signal 14 including an MECG trace, an FECG trace, and noise. It is understood that the placement of the leads 26 may vary to obtain an optimal signal. It is further understood that an optimal signal may be selected from the leads manually or electronically.

Shown in FIG. 1 is a typical placement of electrodes, one lead 26 being placed near the upper right-hand portion of the maternal thoracic region and one lead 26 being placed near the lower left-hand portion of the maternal thoracic region. Another preferred lead placement (not shown) includes the placement of a lead 26 at each of the upper and lower left-hand portions of the maternal thoracic region. The placement of a lead 26 at each of the upper left- and right-hand portions of the maternal thoracic region may alternatively be used. However, this placement selection yields a small amplitude MECG R wave and is difficult to detect for generalized patient types and, therefore, is not preferred.

Under many circumstances non-invasive techniques are inadequate. In those circumstances, invasive techniques may be more practical. Hence, it is sometimes useful for the FECG signal 62 to be obtained by invasive procedures. Provision is made, therefore, for the processing of signals obtained other than by the non-invasive fashion hereinabove described. At least one scalp electrode 32A may be provided to directly obtain the composite signal 14 from the fetus 72. An intrauterine catheter electrode 32B can also be placed in the uterus around the fetus 72 to obtain the composite signal 14.

Figure 6:
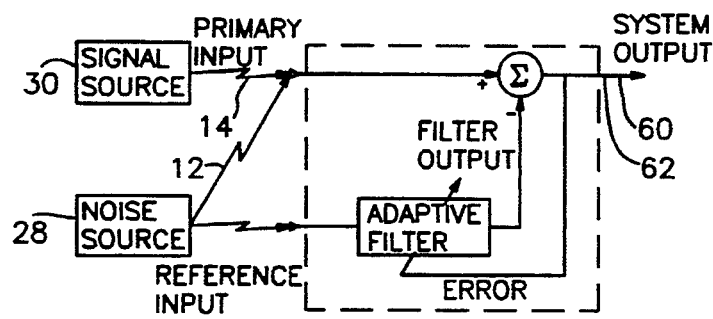
FIG. 6 is a block diagram of a typical adaptive filter.

A preprocessor 34 is provided for processing the signals 12, 14 obtained by the individual electrodes 26 attached to the mother 70 and the fetus 72. The preprocessor 34 is designed to receive and process signals obtained by the non-invasive electrodes 30, the scalp electrode 32A and the intrauterine catheter electrode 32B. When a system with digital capability is employed, the preprocessor 34 digitizes the MECG and composite signals 12, 14. The preprocessor 34 further serves to selectively perform a filtering operation to remove noise and other distortions. This filtering, or signal conditioning, may include adaptive filtering as illustrated in FIG. 6. When using ECG detection means such as a fetal scalp electrode, the preprocessor may not be necessary.

Figure 3A:
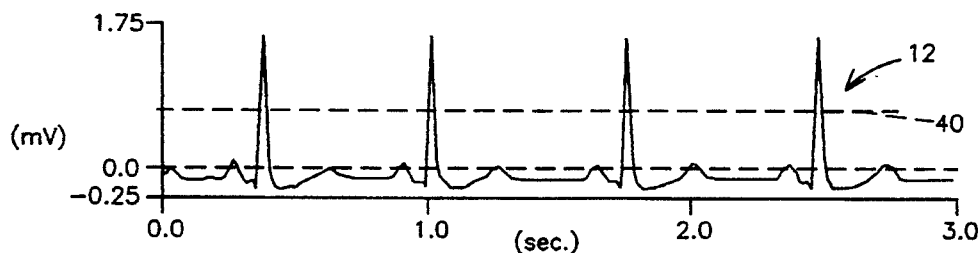
FIG. 3A illustrates a substantially pure MECG signal obtained such as from the thoracic area.
Figure 3B:
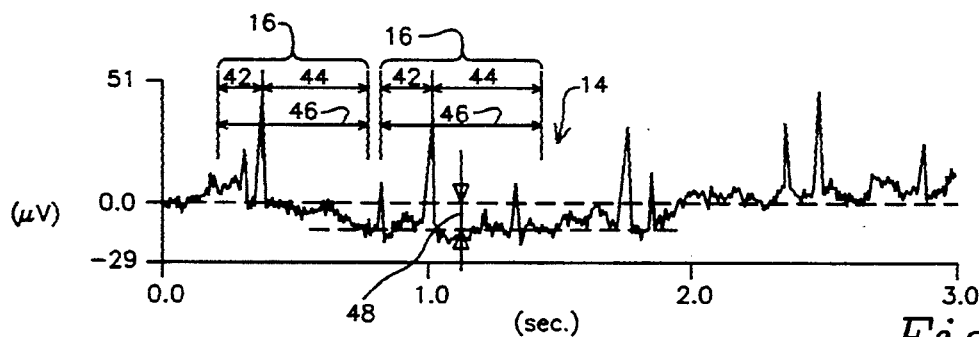
FIG. 3B illustrates a composite ECG signal taken coincidentally with the signal of FIG. 3A including an FECG trace, an MECG trace and noise.
Figure 3C:
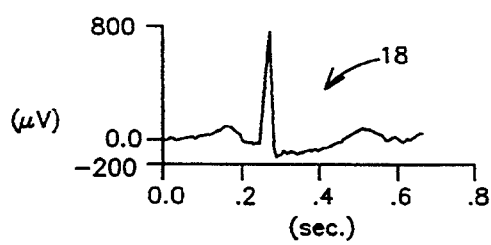
FIG. 3C illustrates an MECG average complex of the composite ECG signal of FIG. 3B using the signal of FIG. 3A as a trigger to align each MECG complex.
Figure 3D:
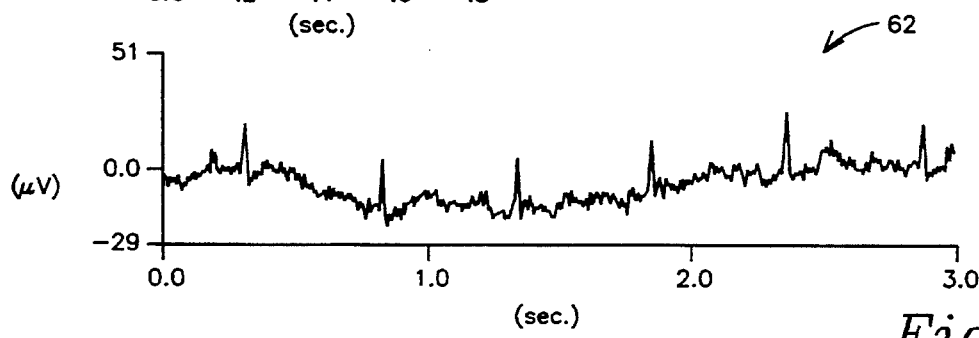
FIG. 3D illustrates an MECG-free trace of the signal of FIG. 3B using the signal of FIG. 3A as a trigger to align the MECG average shown in FIG. 3C for the subtraction.
Figure 4A:
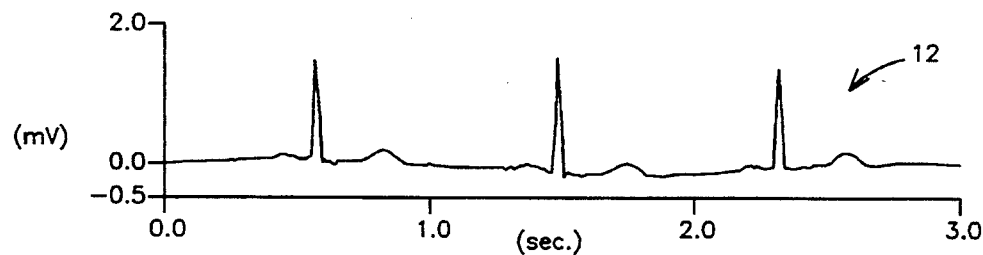
FIG. 4A illustrates a substantially pure MECG signal obtained such as from the thoracic area.
Figure 4B:
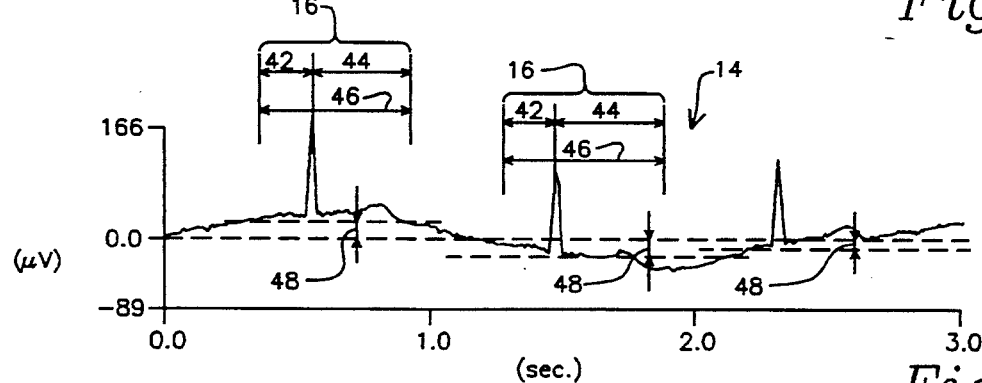
FIG. 4B illustrates a composite ECG signal taken coincidentally with the signal of FIG. 4A including an FECG trace, an MECG trace and noise.
Figure 4C:
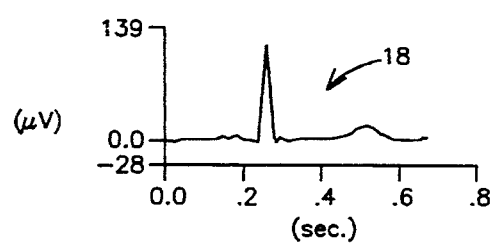
FIG. 4C illustrates an MECG average complex of the composite ECG signal of FIG. 4B using the signal of FIG. 4A as a trigger to align each MECG complex.
Figure 4D:
FIG. 4D illustrates an MECG-free trace of the signal of FIG. 4B using the signal of FIG. 4A as a trigger to align the MECG average shown in FIG. 4C for the subtraction.
Figure 5A:
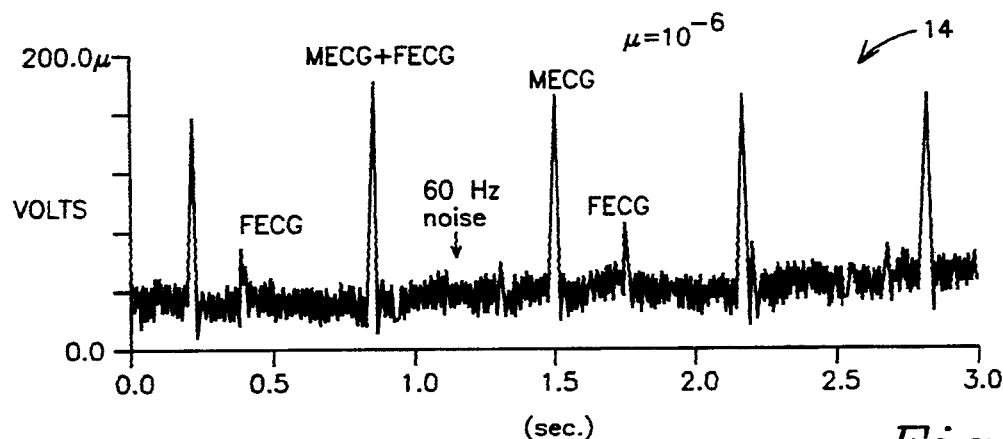
FIG. 5A illustrates an abdominal ECG trace.
Figure 5B:
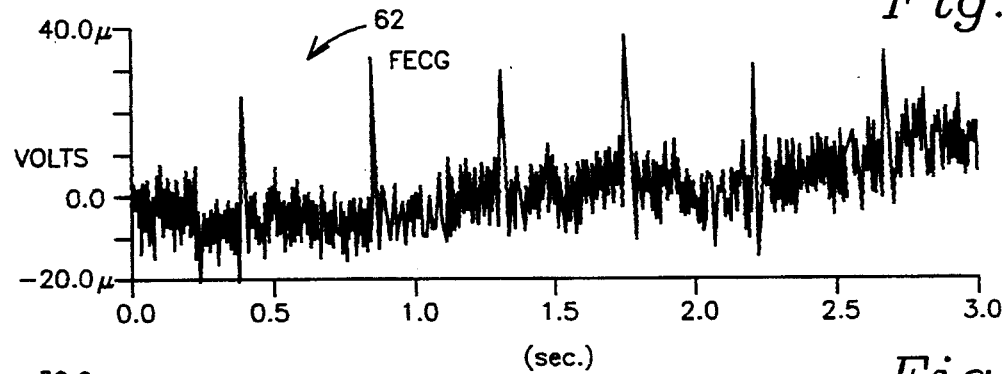
FIG. 5B illustrates a substantially MECG-free abdominal ECG signal using the same procedure used in FIGS. 3A–D and 4A–D.
Figure 5C:
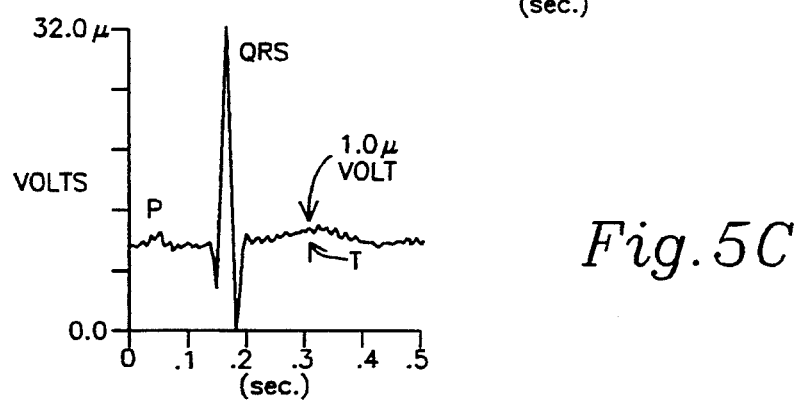
FIG. 5C illustrates an average of several FECG complexes from the signal illustrated in FIG. 5B.

The thoracic MECG signals 12, as shown in FIGS. 3A and 4A, are used as triggers, along with the MECG averages shown in FIGS. 3C and 4C, to obtain the substantially MECG-free FECG signals shown in FIGS. 3D and 4D, respectively. To achieve this objective, a peak detection is performed on the signal 12 to determine the approximate time location of each MECG complex R wave. This is accomplished by determining the maximum amplitude of a portion of the signal 12.

One-half of the maximum signal amplitude, or other appropriate fraction thereof, is used as a threshold for the peak detection, as illustrated at 40 in FIGS. 3A and 4A. As illustrated, the signal 12 is substantially below the threshold 40, except at the occurrence of the MECG R wave. When the signal 12 is increased to a level above the threshold, methods such as an ascending gradient technique or a localized maximum algorithm may be used to determine the local peak of each MECG complex R wave from the time locations determined from the threshold detections. The signals 12, 14 as shown are detected simultaneously.

Using the times transferred from the signal 12 of FIGS. 3A and 4A for each R wave peak, a selected period 46 is chosen for each MECG complex 16 in the composite signal 14. The selected period 46 is defined by moving to the left of the R wave peak a selected distance 42 to include at least the P and Q waves and then by moving to the right a selected distance 44 such as to include at least the S and T waves. The selected period 46 is substantially equal for each MECG complex 16.

The direct current offset 48, or d.c. offset 48, is reduced by averaging the first selected number of samples and the last selected number of samples (generally five to fifteen each) of each detected MECG complex 16 of the composite signal 14, each MECG complex 16 being composed of a series of samples which may be illustrated graphically as shown. The corresponding average of each MECG complex 16 is then subtracted from each sample of the MECG complex 16 before all of the complexes 16 are averaged together.

Next, all of the selected periods 46 are summed and then averaged to yield an MECG complex template 18 as illustrated in FIGS. 3C and 4C. Based on probability and statistics, noise such as electromyographic (EMG) noise or Gaussian noise is reduced by a factor of approximately $n^{\frac{1}{2}}$, where n is the number of selected periods averaged. The FECG component within each period is reduced by a factor of m under the same conditions. Therefore, a greater number of periods studied will most likely yield a greater reduction in noise and a more accurate MECG complex template 18.

The summation of each of the MECG complexes 16 may be improved by a localized correlation of each period of the abdominal MECG complexes in order to determine a better alignment position for averaging. Another localized correlation of the MECG average 18 and each MECG complex 16 may help produce a better subtraction. These two steps may help reduce the residual from the subtraction.

Subtraction methods are used to suppress the MECG trace from the composite signals 14, thus yielding a substantially MECG-free FECG complex 62. The FECG signal-to-noise ratio of the substantially MECG-free FECG complex 62 can be improved through FECG averaging, adaptive filtering and other signal enhancement algorithms. This signal enhancement occurs in the post-processor 64.

It is envisioned that the MECG complex template 18 may be scaled at each MECG complex 16 prior to subtraction in order to cause any residual from the MECG complex template subtraction to be reduced.

It is further envisioned that a plurality of abdominal leads 30,32A,32B may be placed in order to detect more than one composite signal 14. In such a case, the preprocessor 34 and/or the post-processor 64 may be used to determine which of the signals yields the greatest amplitude FECG complexes 62.

Though described as detecting each R wave peak in the substantially pure MECG trace, it will be understood that the method 10 of the present invention is intended to include the detection of any selected point on the MECG complex signal from the MECG trace 12 to be used as a reference point on the composite signal 14.

Further, it will be understood that, though selected arrangements of lead placements have been described as lead placements to detect a substantially pure MECG trace, any arrangement which allows for the detection of a substantially pure MECG trace may be incorporated with the method 10 of the present invention except with the composite MECG+FECG signal 14.

From the foregoing description, it will be recognized by those skilled in the art that a method for suppressing the MECG signal from a composite abdominal ECG including an MECG signal, an FECG signal and noise offering advantages over the prior art has been provided. Specifically, the method provides a means whereby a substantially pure MECG signal may be used as a timing guide to detect the location of a selected point, such as the R wave peak, on each MECG complex within a composite MECG plus FECG plus noise signal. After each of the selected points is determined, averaging methods may be used to find a substantially pure MECG complex template from the composite signal and subtraction methods are performed by subtracting the MECG complex average from the MECG complexes of the composite signal. Thus the yield is a substantially MECG-free FECG signal.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, We claim:

1. A method for suppressing a selected electrocardiograph signal from a composite bio-potential signal including said selected electrocardiograph signal and a selected bio-potential signal, said method comprising the steps of:
   (a) detecting a substantially pure electrocardiograph signal, said substantially pure electrocardiograph signal being defined by a plurality of substantially pure electrocardiograph complexes, each of said plurality of substantially pure electrocardiograph complexes including at least a Q wave, an R wave, and an S wave;
   (b) detecting said composite bio-potential signal substantially simultaneously with said step of detecting said substantially pure electrocardiograph signal;
   (c) determining a time at which a selected point on each of said plurality of substantially pure electrocardiograph complexes occurs;
   (d) indicating said time determined for each of said plurality of substantially pure electrocardiograph complexes at which said selected point occurs on said composite bio-potential signal;
   (e) selecting a plurality of time periods on said composite biopotential signal, each of said plurality of time periods encompassing at least one of said plurality of substantially pure electrocardiograph complexes;
   (f) summing a plurality of portions of said composite bio-potential signal, each of said plurality of portions of said composite bio-potential signal being encompassed by one of said plurality of time periods;
   (g) dividing said summation of said plurality of portions of said composite bio-potential signal corresponding to said plurality of time periods by a number equal to the number of said time periods within said plurality of time periods to produce an electrocardiograph complex template; and
   (h) subtracting said electrocardiograph complex template from said composite bio-potential signal within each of said plurality of time periods.

2. The method of claim 1 wherein said selected electrocardiograph signal is a maternal electrocardiograph signal and said composite bio-potential signal is a composite electrocardiograph signal including at least said maternal electrocardiograph signal and said selected bio-potential signal, said selected bio-potential signal being a fetal electrocardiograph signal.

3. The method of claim 1 wherein said selected point on each of said plurality of substantially pure electrocardiograph complexes is a peak of said R wave.

4. The method of claim 3, after said step of detecting said composite bio-potential signal and before said step of determining a time at which a selected point on each of said plurality of substantially pure electrocardiograph complexes occurs, further comprising the step of determining a maximum value of said substantially pure electrocardiograph signal.

5. The method of claim 4, after said step of determining a maximum value of said substantially pure electrocardiograph signal and before said step of determining a time at which a selected point on each of said plurality of substantially pure electrocardiograph complexes occurs, further comprising the step of determining a threshold level below said peak of said R wave.

6. The method of claim 1 wherein said step of determining a time at which a selected point on each of said plurality of substantially pure electrocardiograph complexes occurs is performed using an ascending gradient technique.

7. The method of claim 1, after said step of selecting a plurality of time periods on said composite bio-potential signal and before said step of summing a plurality of portions of said composite bio-potential signal, further comprising the steps of determining an average direct current offset for each of said plurality of portions of said composite bio-potential signal and subtracting each said average direct current offset from each respective portion of said plurality of portions of said composite bio-potential signal.

8. The method of claim 1, after said step of selecting a plurality of time periods on said composite bio-potential signal and before said step of summing a plurality of portions of said composite bio-potential signal, further comprising the step of correlating each said R wave defined within each of said plurality of portions of said composite bio-potential signal.

9. The method of claim 1, after said step of dividing said summation of said plurality of portions of said composite bio-potential signal corresponding to said plurality of time periods by a number equal to the number of said time periods within said plurality of time periods and before said step of subtracting said electrocardiograph complex template from said composite bio-potential signal within each of said plurality of time periods, further comprising the step of scaling an amplitude defined by said electrocardiograph complex template to substantially correspond with an amplitude defined by each of said plurality of portions of said composite bio-potential signal.

10. A method for suppressing a maternal electrocardiograph signal from a composite electrocardiograph signal including said maternal electrocardiograph signal and a fetal electrocardiograph signal, said method comprising the steps of:

(a) detecting a substantially pure maternal electrocardiograph signal, said substantially pure maternal electrocardiograph signal being defined by a plurality of substantially pure maternal electrocardiograph complexes, each of said plurality of substantially pure maternal electrocardiograph complexes including at least a Q wave, an R wave, and an S wave;

(b) detecting said composite electrocardiograph signal substantially simultaneously with said step of detecting said substantially pure maternal electrocardiograph signal;

(c) determining a maximum value of said substantially pure maternal electrocardiograph signal;

(d) determining a threshold level below a selected point;

(e) determining a time at which said selected point on each of said plurality of substantially pure maternal electrocardiograph complexes occurs;

(f) indicating said time determined for each of said plurality of substantially pure maternal electrocardiograph complexes at which said selected point occurs on said composite electrocardiograph signal;

(g) selecting a plurality of time periods on said composite electrocardiograph signal, each of said plurality of time periods encompassing at least one of said plurality of substantially pure maternal electrocardiograph complexes;

(h) summing a plurality of portions of said composite electrocardiograph signal, each of said plurality of portions of said composite electrocardiograph signal being encompassed by one of said plurality of time periods;

(i) dividing said summation of said plurality of portions of said composite electrocardiograph signal corresponding to said plurality of time periods by a number equal to the number of said time periods within said plurality of time periods to produce a maternal electrocardiograph complex template; and (j) subtracting said maternal electrocardiograph complex template from said composite electrocardiograph signal within each of said plurality of time periods.

11. The method of claim 10 wherein said selected point on each of said plurality of substantially pure maternal electrocardiograph complexes is a peak of said R wave.

12. The method of claim 10 wherein said step of determining a time at which a selected point on each of said plurality of substantially pure maternal electrocardiograph complexes occurs is performed using an ascending gradient technique.

13. The method of claim 10, after said step of selecting a plurality of time periods on said composite electrocardiograph signal and before said step of summing a plurality of portions of said composite electrocardiograph signal, further comprising the steps of determining an average direct current offset for each of said plurality of portions of said composite electrocardiograph signal and subtracting each said average direct current offset from each respective portion of said plurality of portions of said composite electrocardiograph signal.

14. The method of claim 10, after said step of selecting a plurality of time periods on said composite electrocardiograph signal and before said step of summing a plurality of portions of said composite electrocardiograph signal, further comprising the step of correlating each said peak of said R wave defined within each of said plurality of portions of said composite electrocardiograph signal.

15. The method of claim 10, after said step of dividing said summation of said plurality of portions of said composite electrocardiograph signal corresponding to said plurality of time periods by a number equal to the number of said time periods within said plurality of time periods and before said step of subtracting said maternal electrocardiograph complex template from said composite electrocardiograph signal within each of said plurality of time periods, further comprising the step of scaling an amplitude defined by said maternal electrocardiograph complex template to substantially correspond with an amplitude defined by each of said plurality of portions of said composite electrocardiograph signal.

16. A method for suppressing a maternal electrocardiograph signal from a composite electrocardiograph signal including said maternal electrocardiograph signal and a fetal electrocardiograph signal, said method comprising the steps of:

(a) detecting a substantially pure maternal electrocardiograph signal, said substantially pure maternal electrocardiograph signal being defined by a plurality of substantially pure maternal electrocardiograph complexes, each of said plurality of substantially pure maternal electrocardiograph complexes including at least a Q wave, an R wave, and an S wave;

(b) detecting said composite electrocardiograph signal substantially simultaneously with said step of detecting said substantially pure maternal electrocardiograph signal;

(c) determining a maximum value of said substantially pure maternal electrocardiograph signal;

(d) determining a threshold level below a selected point;

(e) determining a time at which said selected point on each of said plurality of substantially pure maternal electrocardiograph complexes occurs;

(f) indicating said time determined for each of said plurality of substantially pure maternal electrocardiograph complexes at which said selected point occurs on said composite electrocardiograph signal;

(g) selecting a plurality of time periods on said composite electrocardiograph signal, each of said plurality of time periods encompassing at least one of said plurality of substantially pure maternal electrocardiograph complexes;

(h) determining an average direct current offset for each of said plurality of portions of said composite electrocardiograph signal;

(i) subtracting each said average direct current offset from each respective portion of said plurality of portions of said composite electrocardiograph signal;

(j) correlating each said time of occurrence of each said selected point defined within each of said plurality of portions of said composite electrocardiograph signal;

(k) summing a plurality of portions of said composite electrocardiograph signal, each of said plurality of portions of said composite electrocardiograph signal being encompassed by one of said plurality of time periods;

(l) dividing said summation of said plurality of portions of said composite electrocardiograph signal corresponding to said plurality of time periods by a number equal to the number of said time periods within said plurality of time periods to produce a maternal electrocardiograph complex template;

(m) scaling an amplitude defined by said maternal electrocardiograph complex template to substantially correspond with an amplitude defined by each of said plurality of portions of said composite electrocardiograph signal; and (n) subtracting said maternal electrocardiograph complex template from said composite electrocardiograph signal within each of said plurality of time periods.

17. The method of claim 16 wherein said selected point on each of said plurality of substantially pure maternal electrocardiograph complexes is a peak of said R wave.

18. The method of claim 16 wherein said step of determining a time at which a selected point on each of said plurality of substantially pure maternal electrocardiograph complexes occurs is performed using an ascending gradient technique.

* * * * *